US00PP21771P2

(12) United States Plant Patent
Hurd

(10) Patent No.: US PP21,771 P2
(45) Date of Patent: Mar. 8, 2011

(54) ***ECHINACEA* PLANT NAMED 'ALL THAT JAZZ'**

(50) Latin Name: ***Echinacea* hybrid**
Varietal Denomination: All that Jazz

(75) Inventor: Kevin A. Hurd, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 231 days.

(21) Appl. No.: 12/231,683

(22) Filed: Sep. 5, 2008

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP16,235 P2 * 2/2006 Saul ..... Plt./428

OTHER PUBLICATIONS

*Echinacea* 'All That Jazz' PPAF CPBRAF available at http:// www.waltersgardens.com.*
Google image search for 'All That Jazz'.*
*Echinacea* 'All that Jazz' from Coneflower.com available at http://www.coneflower.com 2008/12/echinacea-all-that-jazz.html.*

* cited by examiner

*Primary Examiner*—Wendy Haas

(57) ABSTRACT

The new and distinct cultivar of Coneflower, *Echinacea* plant named 'All that Jazz', with fragrant flowers on strong stems having quilled ray petals of pinkish lavender and orange cones over at least 10 weeks from mid-summer into fall and vigorous growth habit.

2 Drawing Sheets

Botanical denomination: *Echinacea* hybrid.

Cultivar designation: 'All that Jazz'.

BACKGROUND OF THE INVENTION

The present invention relates to the new and distinct cultivar of Coneflower from the genus *Echinacea* and given the cultivar name 'All that Jazz'. The new plant was the result of an intentional cross between *Echinacea* 'Sunrise' U.S. Plant Pat. No. 16,235 and an unpatented proprietary hybrid known as #04-02-08 on Oct. 3, 2005 at a nursery in Zeeland, Mich., USA. This seedling originally named #05-17-01 and later named 'All that Jazz' was selected for further evaluation and production trials during the summer of 2007. *Echinacea* 'All that Jazz' has been asexually propagated at the same nursery in Zeeland, Mich. using careful tissue culture multiplication procedures and found to reproduce plants that exhibit all the characteristics identical to the original plant.

Compared to other known Coneflowers, some may have similar colored flowers and similar plant heights and habits, but none have the consistently quilled ray petals of 'All that Jazz.' The new plants can be compared to 'Kim's Knee High' U.S. Plant Pat. No. 12,242 and 'Ruby Giant' (unpatented). 'All that Jazz' is taller than 'Kim's Knee High' and similar in height to 'Ruby Giant'. 'Ruby Giant' also has a larger diameter flower with flattened rather than quilled petals of the new plant. 'Kim's Knee High' is shorter with flattened petals that droop more from the edge of the cone, unlike 'All that Jazz' which has quilled and horizontal petals. *Echinacea* 'Fatal Attraction' U.S. Plant Pat. No. 18,429 has darker purple petals that are flattened compared to the quilled and lighter lavender pink petals of 'All that Jazz'. 'Fatal Attraction' is also about 10 cm shorter than 'All that Jazz'.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant flowers on strong stems.
2. Horizontal lavender ray petals with orange cone.
3. Ray petals quilled or rolled except at apex.
4. Vigorous growth and excellent habit.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
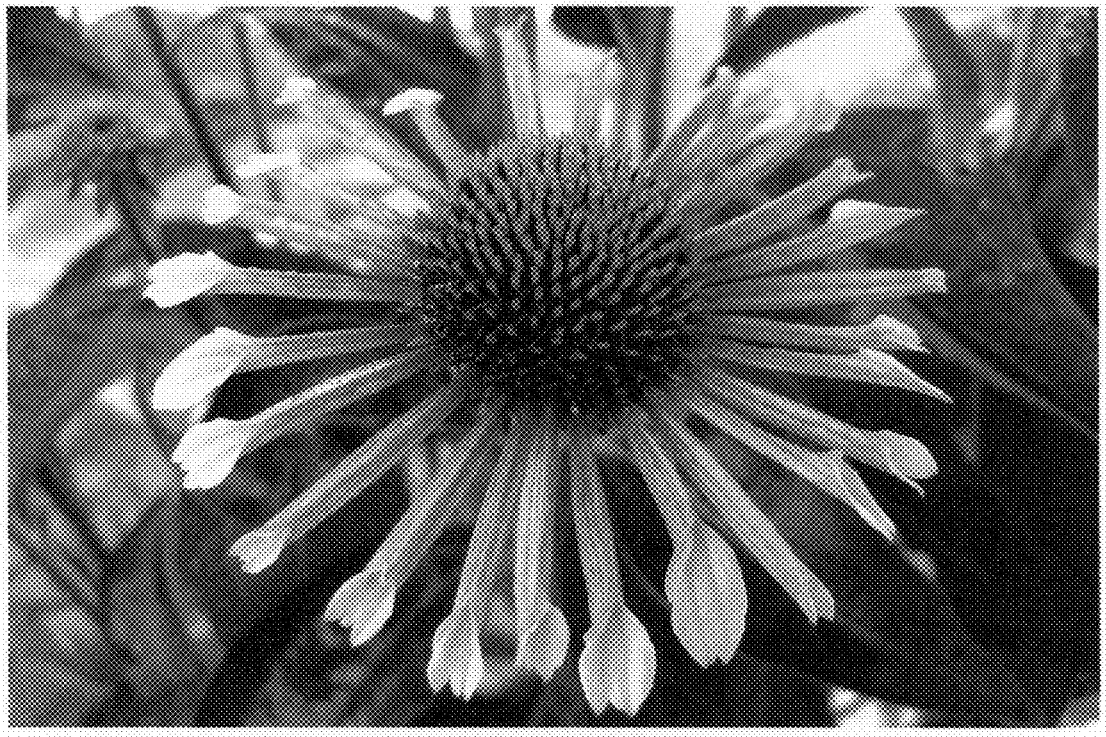
FIG. 1 shows a close up of a flower of the new plant.
Figure 2:
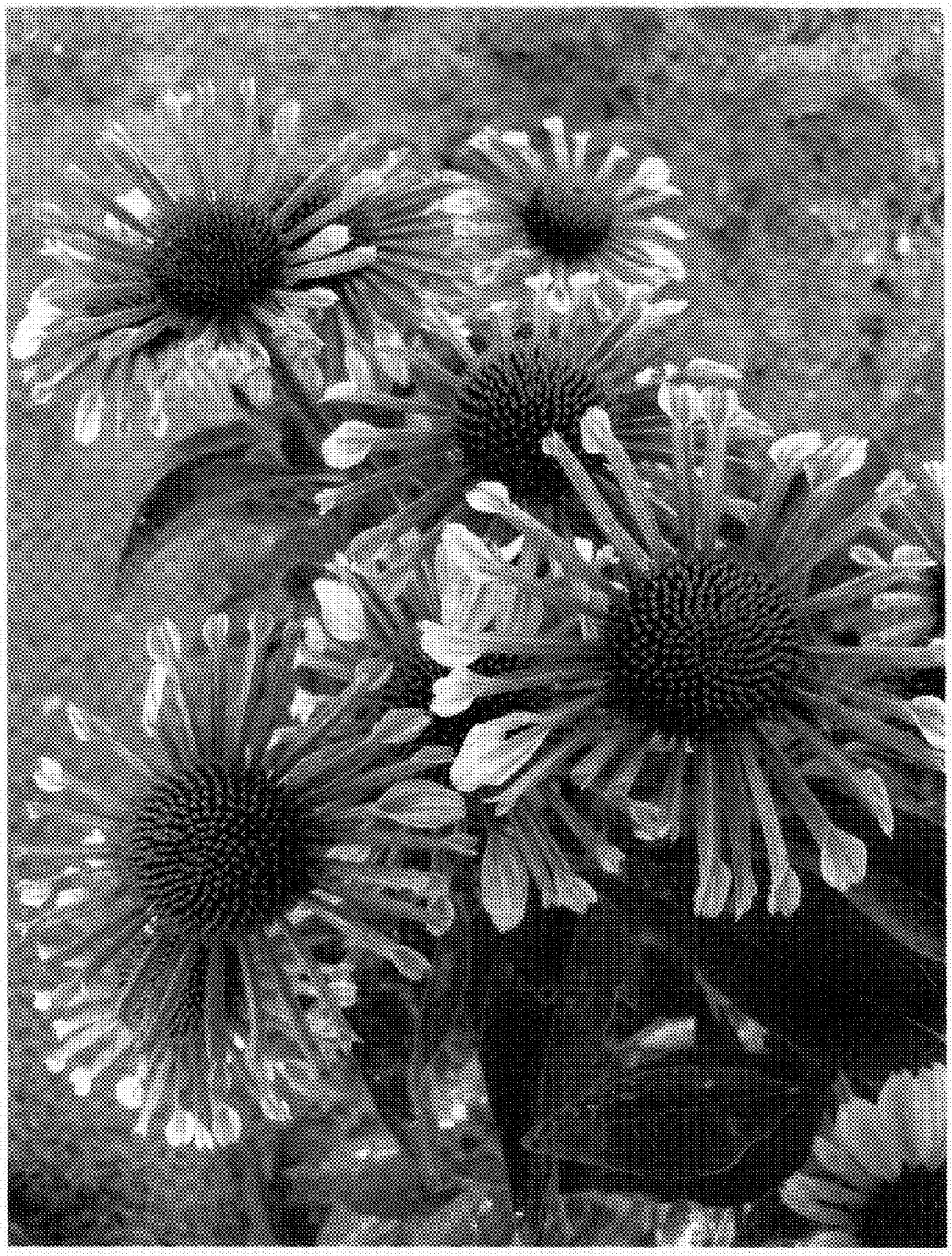
FIG. 2 shows the habit of the new plant in flower.

The following description of *Echinacea* 'All that Jazz' is based on observations of two-year old specimens grown in a full sun trial garden with supplemental water and fertilizer in Zeeland, Mich. The new plant has not been tested in all environments and some phenotypic differences may occur with different environments without, however, any change in genotype. The color descriptions are based on the 2001 edition of The Royal Horticultural Society Colour Chart except where common dictionary descriptions are used.

Parentage: Female *Echinacea* 'Sunrise' U.S. Plant Pat. No. 16,235, male proprietary unreleased hybrid #04-08-02;

Plant habit: Multi-stemmed, freely-branched, hardy herbaceous perennial, flowering to about 90 cm tall and 65 cm wide;

Growth rate: Vigorous, finishing in 4 liter containers in about 2 months during the summer;

Roots: Cream-colored, finely branched;

Foliage: Alternate, lanceolate, acute apex, attenuate base, dentate, hirtellous both surfaces, lower leaves largest and distal leaves decreasing in size; largest leaves about 25 cm long and 10 cm wide, upper most leaves about 8 cm long and 2 cm wide; between RHS 136 A and RHS 136B above and RHS 137B beneath;

Venation: Arcuate with two major veins on both sides of the center vein; center vein protruding 2 mm below bottom surface of leaf, other major veins protruding about 1 mm below bottom leaf surface; RHS 145D underneath and closest to RHS 145D above;

Petiole: Hirtellous, concave, about 18 cm long and 2.5 mm wide on lowest leaves and decreasing on upper leaves to sessile; underneath nearest RHS145D with stipules of RHS 138A and slight tinting in areas exposed to bright light of RHS 75B;

Peduncle: Sparsely hirtellous, average 8 mm diameter and average 85 cm tall;

Pedicel: Sparsely hirtellous, average 4 mm diameter and 10 cm long;

Inflorescence: Bracteate head, aggregate of achene; with distinct ligulate ray florets and disk florets in a pappus; beginning mid-July and continuing until frost; initial flowers largest, average flower size 10 cm diameter with cones 3.5 cm across and 3 cm tall; approximately 15 flowers per peduncle; sweetly fragrant;

Flower persistence: Remaining affective in color for 10 to 14 days depending on temperatures, drying on plant with cones effective into winter:

Involucre: With numerous bracts, about 96 per flower; curved downward toward pedicle;

Bracts: Lanceolate, entire, narrowly acute; to 1 cm long and 2 mm wide; RHS 137A;

Ray florets: Petals emarginated, 24 to 28 per flower; opening to horizontal, not drooping beyond horizontal; average size 3.5 cm long, 4 cm wide at center tapering to 2 mm wide at base; proximal 75% to 90% of ray petal curled into tube (quilled) with the distal end of between 3 to 15 mm opened; open portion between 3 to 9 mm wide and RHS 75D; underside of quilled petals lighter than RHS 75D; pollen not observed;

Disc florets: Outer florets about 8 mm long and 2 mm wide, RHS 143C near base of petal and RHS 145D near apex of petal; central florets about 11 mm long and 2 mm wide; RHS 144C near base of petal and RHS 146A at apex;

Disk floret androecium: Stamen column about 1 mm wide and protrudes from petals about 2 mm, RHS N77C; pollen attached to column by thin filaments of RHS 59A, globose, less 0.1 mm in diameter, RHS 17C;

Pappus: With numerous bristles; bristles about 13 mm long and 1 mm wide; RHS 53A at apex terminal 1 mm followed by RHS N25B below the tip and for the next 2 mm, with the next 4 mm RHS 144A and lightening to the distal portion of lighter than RHS 145D;

Bud: With ray petals still upright—petals to 2.5 cm long and 3 mm wide at center; lighter than RHS 62D with slight greenish tint at apex, center of petal between RHS 63B and RHS 63C, base of petal nearest RHS 150 B;

*Fruit.*—Achene; about 4 mm long and 2 mm wide; between RHS 199A and RHS 199B;

Disease resistance: Resistance beyond that of other hardy Coneflower cultivars has not been observed. The plant grows best with plenty of moisture and adequate drainage, but is able to tolerate some drought when mature. Hardiness at least from USDA zone 4 through 8.

I claim:

1. A new and distinct cultivar of Coneflower, *Echinacea* plant named 'All that Jazz' as herein described and illustrated, with quilled ray petals of pinkish lavender over at least 10 weeks from mid-summer into fall, and suitable as a potted plant, for the garden, and for cut flower arrangements.

* * * * *